United States Patent [19]

Wendt

[11] Patent Number: 5,033,318

[45] Date of Patent: Jul. 23, 1991

[54] APPARATUS FOR MEASURING THE PARTICULATE CONTAMINATION IN FLUES CONTAINING CORROSIVE DUSTS

[75] Inventor: Horst Wendt, Erlangen, Fed. Rep. of Germany

[73] Assignee: FAG Kugelfischer Georg Shafer, Kommanditgesellschaft, Fed. Rep. of Germany

[21] Appl. No.: 503,260

[22] Filed: Apr. 2, 1990

[30] Foreign Application Priority Data

Apr. 1, 1989 [EP] European Pat. Off. ........ 89105780.4

[51] Int. Cl.$^5$ ................................................. G01N 1/00
[52] U.S. Cl. ................................................. 73/863.03
[58] Field of Search ........... 73/863.02, 863.03, 863.11, 73/863.23, 863.24, 863.83, 863.34, 864.73, 861.65, 28.03, 28.04; 55/270

[56] References Cited

U.S. PATENT DOCUMENTS

| | | | |
|---|---|---|---|
| 3,380,298 | 4/1968 | Hanson | 73/861.65 |
| 3,473,388 | 10/1969 | Lynn | 73/863.03 |
| 3,784,902 | 1/1974 | Huber | 73/863.03 |
| 3,793,887 | 2/1974 | Anderson et al. | 73/863.03 |
| 3,824,395 | 7/1974 | Fries et al. | 250/308 |
| 4,578,986 | 4/1986 | Navarre | 73/863.24 |
| 4,611,488 | 9/1986 | Weingart | 73/861.65 |

OTHER PUBLICATIONS

Solnick, "Sampling Particulate Matter", The Oil and Gas Journal, Oct. 1956, pp. 120–124.

Primary Examiner—Robert Raevis
Attorney, Agent, or Firm—Ostrolenk, Faber, Gerb & Soffen

[57] ABSTRACT

An apparatus for measuring the dust contamination in flues containing corrosive dusts, particularly chimneys, in which an equal-velocity or isokinetic removal of a sample stream of gas takes place and the sample stream of gas is mixed with fresh air to reduce the dew point and fed to the evaluation filter.

13 Claims, 1 Drawing Sheet

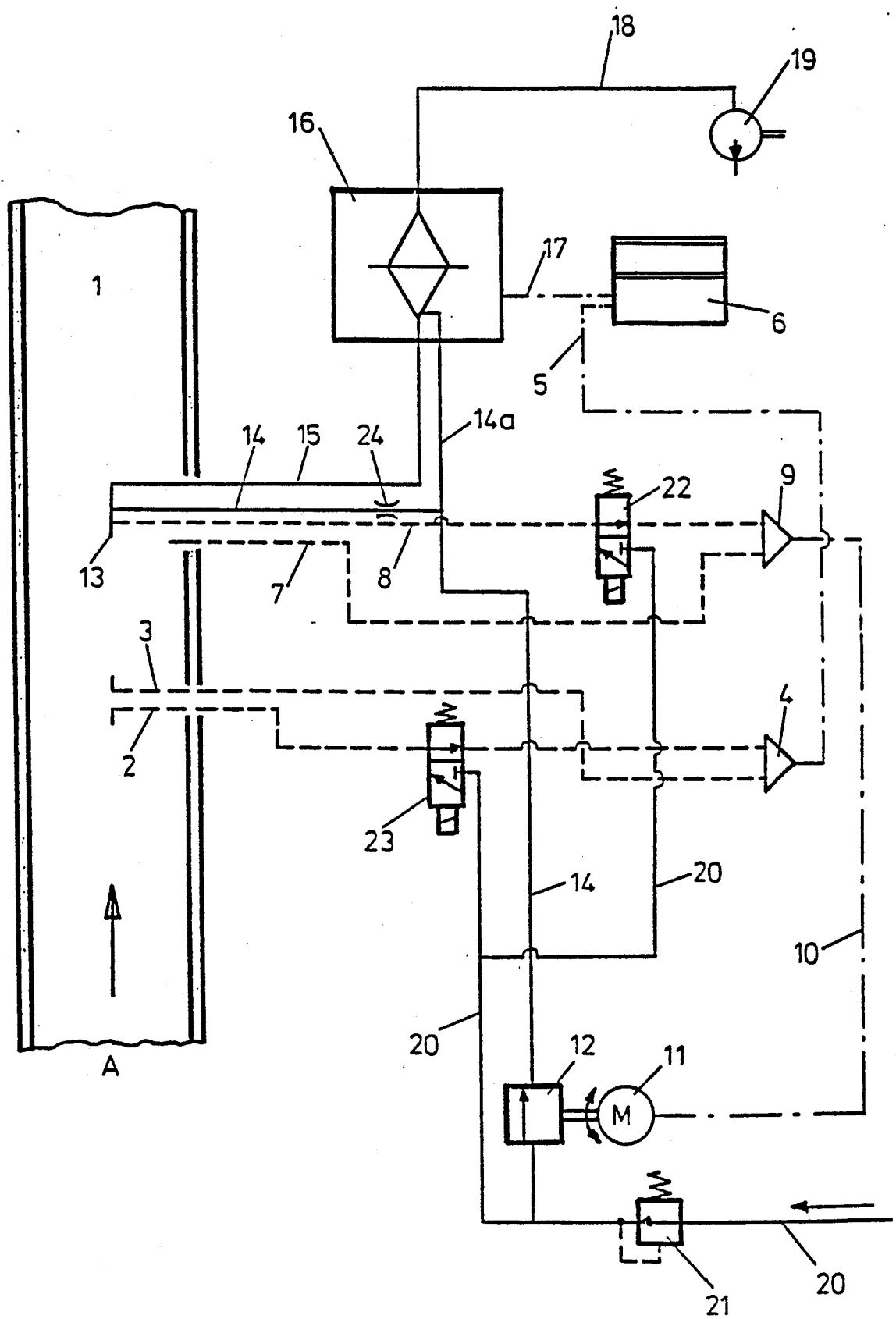

APPARATUS FOR MEASURING THE PARTICULATE CONTAMINATION IN FLUES CONTAINING CORROSIVE DUSTS

BACKGROUND OF THE INVENTION

The present invention relates to a device for measuring the particulate content of gas, which may contain corrosive dusts from a stationary source, like a flue, as in a chimney, in which an equal velocity or isokinetic removal of a sample stream of gas takes place and the sample stream of gas is mixed with fresh air and is fed to an evaluation filter.

Embodiments of this type of device are disclosed in German Patents 20 32 127 and 22 37 736. Those embodiments, however, have several disadvantages. First, the throttles of the device become dirty very rapidly. Secondly, during operation, deposits form on the shafts of the pneumatic controllers, resulting in very expensive maintenance and down time of the measuring devices. Therefore, rubbish incineration plants, which must be operated with emissions measurement, must be shut down during maintenance. Furthermore, in known devices, there is a danger of the measurement diaphragms icing if the outside temperatures fluctuate around the freezing point. Due to maintenance requirements, the percentage of availability of these devices is less than 90%. Finally, the control response of these devices is sluggish.

SUMMARY OF THE INVENTION

It is the object of the present invention to create an emission measurement device which has reduced down time for maintenance.

In accordance with the inventive concept the gas flow velocity in the flue is sampled and that information is fed via pitot tubes to a pressure difference meter which may be in the form of an analog amplifier. The volumetric flow of flue gas can then be displayed or recorded in cubic meters via a computer or other monitoring device coupled to the pressure difference meter. At the same time the weight of the dust which has collected from the sampled gas and on an evaluation filter is determined and this measured value is fed to the computer for display or recording.

The apparatus includes a flue gas removal nozzle located in the flue for removing some of the flue gas. Suction means are connection with the nozzle for sucking air and flue gas at a constant velocity through a first conduit. There is a filter in the first conduit that collects particulate material from the flue gas. Although such a nozzle is described herein, details of a particular embodiment nozzle are disclosed in European Application 89 105 779.6, filed Apr. 1, 1989, corresponding to U.S. Ser. No. 07/503,523, filed Apr. 2, 1990. There are means that measure the build up of particulate material on the filter over time. There is a compressed gas supply that communicates to the first conduit, particularly in the vicinity of the suction nozzle, thereby supplying compressed gas to the nozzle so that the first conduit can suction flue gas, compressed gas or a mixture thereof. A valve in the second conduit from the gas supply controls the flow rate of compressed gas to the first conduit.

A first pressure sensor in the flue near the suction nozzle senses the essentially static pressure in the flue. A second pressure sensor generally located at the nozzle and in the first conduit senses the essentially static pressure at the nozzle upstream of the connection of the second conduit from the gas supply to the first conduit. A pressure difference sensing means is connected to the first and second sensors. When it senses a difference in the pressure, it operates a valve to deliver gas from the gas supply to the nozzle at the first conduit for mixing gas with flue gas extracted by the nozzle from the flue. The flow rate of the gas from the gas supply into the first conduit at the nozzle is regulated to cause the first and second sensors to sense a set ratio of pressure, particularly the same pressure, so that the sensed pressure difference is zero. When the pressure difference is zero, then the velocity of the gas in the sampling nozzle is identical to the velocity of the gas in the stack, providing isokinetic sampling. The removal nozzle will now remove flue gas from the flue at a rate dependent upon the velocity of the stream of gas in the flue while the flow through the first conduit remains at a constant velocity.

There is also a flue gas velocity rate measuring means in the flue. A computer connected with both the filter build up measuring means and the flue gas velocity measuring means can combine that information to supply an indication of the concentration of particulate material in the flue gas per unit of volume of the flue gas, e.g. milligrams of particulate material per cubic meter of flue gas.

To keep the objects which can be contaminated with particulate material clean, there is a third conduit for compressed gas from the gas supply to the removal nozzle and operable by a valve for periodically blowing out the removal nozzle for cleaning it. There is also a fourth conduit for compressed gas from the gas supply to the flow rate measuring means and operable by a valve for periodically blowing to clean the flow rate measuring means.

The flue gas flow rate measuring means will comprise at least one tube facing to receive the flow of gas from the upstream direction. Preferably, it also includes a second tube facing counter to the flow of gas and a comparison means for comparing the pressures at the first and second tubes for computing the velocity of the flue gas. The means for delivering compressed gas to the flow rate measuring means would deliver the gas to the tube facing upstream in the flow path of the flue gas for cleaning the particulate materials.

Finally, a conduit from the gas supply helps clean the filter.

BRIEF DESCRIPTION OF THE DRAWING

The objects and features of the invention are explained with reference to the drawing which shows schematically an apparatus according to the invention.

DESCRIPTION OF A PREFERRED EMBODIMENT

Referring to the drawing, a flue 1 is shown, in which dust laden outgoing air or gas flows in the direction indicated by the arrow A. Flow velocity measuring pitot tubes 2 and 3, schematically shown by respective dotted lines, extend into flue 1. Tube 2 is conventionally arranged so that its inlet is against the direction of gas flow, and tube 3 is conventionally arranged so that its inlet is in the direction of gas flow. Tubes 2 and 3 are connected to a pressure difference meter 4. The pressure difference meter 4 is connected via the signal lines 5 to a suitable computer 6 so that the rate of outgoing gas moving through the flue, for example, in cubic meters per second, can be displayed and/or recorded by the computer 6.

Also extending into the flue 1 is a static pressure tube 7 and a zero pressure tube 8. For assuring that a constant quantity of flue gas is removed for sampling, regardless of the gas velocity, the pressures at pressure tubes 7 and 8 should be at a particular ratio, e.g. the same pressure. The pressure tubes 7 and 8 are also connected to the inputs of a second pressure difference meter 9. The pressure difference meter 9 is connected via the signal line 10 to the valve actuating means 11, which is for instance, a motor or solenoid for opening or closing the valve 12 depending upon the signals received from the pressure difference meter 9.

The zero pressure tube 8, a fresh air flush tube 14 and a sample removal tube 15 are all connected to a removal suction nozzle 13 which extends into the flue 1.

The removal tube 15 leads to a known type of dust measurement filter 16. Filter 16 is in communication via the signal lines 17 with the computer 6 in such a manner that the amount of dust weighed in the dust measurement filter 16 can be displayed and/or recorded by the computer 6, for example, in milligrams. Because the means 4 and 6 described above measures the velocity of the flue of the flue gas, the computer can state the weight of collected particulate material in milligrams per cubic meter of outgoing air.

A part of the outgoing air present in the flue 1 is drawn in by the suction unit 19 via the removal nozzle 13, removal tube 15, dust measurement filter 16, and suction line 18. The suction device 19 can be an ordinary vacuum pump.

Compressed air line 20 is connected to the valves 12, 22 and 23 by a known pressure reduction valve 21.

Within the removal nozzle flush tube 14, which extends from the valve 12 to the removal nozzle 13, is the throttle 24. From the tube 14, a branch tube 14a leads to the dust measurement filter 16. The flow from the tube 14a under control of the valve 12 flushes a titanium filter inserted at the filter 16 for protecting the measurement device from becoming dirty.

The operation of this device is described, first assuming that the velocity of flow of the outgoing air in the flue 1 is zero, the suction device 19 is connected and fresh air or compressed air is available in the compressed air line 20.

The suction device 19 draws outgoing air from flue 1 via suction line 18, dust measurement filter 16, and removal tube 15. At the same time, fresh air flows under pressure, with valve 12 open, over flush tube 14 to the outlet at the removal nozzle 13. As a result, a vacuum is produced in the zero pressure tube 8 with respect to the static pressure tube 7. The pressure difference meter 9 "recognizes" these pressure conditions and, via signal line 10, gives "open signals" to the valve actuating means 11 which now opens the valve 12 until the difference of pressure in the tubes 7 and 8 is equal to zero. As soon as this zero pressure difference is reached, the same amount of fresh air or compressed air that is being drawn out in the removal tube 15 flows through the flush tube 14 so that no outgoing air is removed from flue 1 through nozzle 13. Now, the apparatus has been zeroed for flue gas flow operation.

If the velocity of the outgoing air in flue 1 is greater than zero, then elevated pressure is produced in the zero pressure tube 8 with respect to the static pressure tube 7. As a result, the pressure difference meter 9 forces the valve 12 to close which reduces the air flow through the flush tube 14 until the pressure difference between the tubes 7 and 8 is equal to zero. Because the suction device 19 draws at a constant rate while the air flow supplied from flush tube 14 has been reduced, a partial stream of flue gas is drawn off at the removal nozzle 13 related to the velocity of flow prevailing in the flue. At a higher velocity of flow, the pressure difference between tubes 7 and 8 is greater, the flush air flow is smaller and more of the mixed gas stream is comprised of flue gas. Therefore, the amount of particulate material collected on the filter 16 per unit of time is dependent upon the flue gas velocity in the flue and upon the concentration of particulate material in the flue gas.

With this invention, an equal velocity or isokinetic removal of a partial stream of gas always takes place. A partial stream of gas which consists of a mixture of outgoing flue gas and fresh air is drawn by the suction device 19 through the dust measurement filter 16. The dust deposited in the dust measurement filter 16 is determined continuously by determination of the weight of particulates coupled with the flow velocity measurement values fed to the computer 6, this can produce a measure of particulate concentration be stated in terms of milligrams of particulates per cubic meter of gas.

In order that no condensate forms within this device, both the flush tube 14 and the removal tube 15 are heated to a temperature above that of the corresponding dew point of the gases passing through them.

The tubes 2 and 8 as well as removal nozzle 13 are cleaned by being blown out in a selectable or predeterminable cycle by the selected periodic opening of the normally closed valves 22 and 23.

Although the present invention has been described in relation to a particular embodiment thereof, many other variations and modifications and other uses will become apparent to those skilled in the art. It is preferred, therefore, that the present invention be limited not by the specific disclosure herein, but only by the appended claims.

What is claimed is:

1. Apparatus for measuring the particulate content of gas moving through a flue comprising:
   a flue gas removal nozzle in the flue for removing some of the flue gas from the flue; suction means, a first conduit communicating between the nozzle and the suction means for conducting flue gas through the nozzle to the suction means;
   means including a filter in the first conduit for collecting particulate material from the flue gas being drawn through the first conduit by the suction means and for measuring the buildup of particulate material on the filter over time;
   a compressed gas supply, a second conduit between the gas supply and the first conduit, a first valve in the second conduit selectively openable for controlling the flow rate of compressed gas to the first conduit;
   a first pressure tube in the flue near the suction nozzle for sensing the pressure in the flue, a second pressure tube generally at the nozzle for sensing the pressure in the nozzle upstream of the connection to the first conduit of the second conduit; pressure difference measuring means connected to the first and second pressure tubes for sensing the pressure difference between them; the pressure difference measuring means being connected with the first valve for operating the first valve to selectively deliver gas pressure to the second conduit until the pressures at the first and second pressure sensors are in a preset relationship, whereby the removal nozzle will remove flue gas at a rate dependent upon the velocity of the stream of gas in the flue while the flow through the first conduit downstream of the connection of the first conduit to the second conduit is at a constant velocity;

flue gas flow rate measuring means in the flue for measuring the velocity of the flue gas in the flue.

2. The apparatus of claim 1, further comprising first means for delivering compressed gas to the removal nozzle for blowing out the removal nozzle for cleaning it and second means for delivering compressed gas from the gas supply to the flow rate measuring means for cleaning the flow rate measuring means.

3. The apparatus of claim 2, wherein the flue gas flow rate measuring means comprises at least a first tube having an inlet exposed to the flowing flue gases, and the second means for delivering compressed gas comprises a valve communicating with the tube of the flow rate measuring means, the valve being selectively openable for selectively delivering compressed gas to the tube for cleaning the tube.

4. The apparatus of claim 3, wherein the first tube of the flue gas flow rate measuring means communicates upstream in the flow of flue gases; the flue gas flow rate measuring means further comprising a second tube having an inlet communicating downstream in the flue and in the flow of flue gas; a second pressure difference measuring means connected between the first and second tubes for determining the flue gas flow velocity past the flue gas flow rate measuring means from the pressure difference between them.

5. The apparatus of claim 4, wherein the second means for delivering compressed gas comprises a third valve connected with the gas supply for selectively delivering a compressed gas cleaning flow to the first tube of the flow rate measuring means.

6. The apparatus of claim 5, wherein the first means for delivering compressed gas to the removal nozzle comprises a third conduit from the gas supply to the removal nozzle and a valve in the third conduit which valve is selectively openable.

7. The apparatus of claim 4, further comprising a computer for receiving information from the second pressure difference measuring means and for computing the flue gas flow velocity.

8. The apparatus of claim 7, wherein the means for collecting particulate matter and measuring the buildup of particulate matter on the filter is connected with the computer for continuously determining and recording the weight of the deposit of particulate material on the filter, and the computer being adapted for combining the flow velocity of the flue gas with the change in the weight of deposited particulate material for indicating the quantitative value of the particulate material deposited on the filter per quantity of flue gas.

9. The apparatus of claim 8, wherein the first valve is operable for delivering gas pressure to the second conduit until the pressures at the first and second pressure tubes are equal.

10. The apparatus of claim 2, wherein the first means for delivering compressed gas to the removal nozzle comprises a third conduit from the gas supply to the removal nozzle and a valve in the third conduit which valve is selectively openable.

11. The apparatus of claim 10, wherein the third conduit communicates with the nozzle through the second pressure tube.

12. The apparatus of claim 2, wherein the first means for delivering compressed gas to the removal nozzle includes flush conduit and the flush conduit and the first conduit for removal of flue gas are both heated to be above the temperature of the corresponding dew point.

13. The apparatus of claim 2, wherein the first valve is operable for delivering gas pressure to the second conduit until the pressures at the first and second pressure tubes are equal.

* * * * *